United States Patent [19]

Nakai et al.

[11] Patent Number: 4,935,240
[45] Date of Patent: Jun. 19, 1990

[54] BENZOYLAMINOPHENOXYBUTANOIC ACID DERIVATIVES

[75] Inventors: Hisao Nakai; Hiroshi Terashima, both of Takatsuki; Yoshinobu Arai, Osaka, all of Japan

[73] Assignee: Ono Pharmaceutical Co., Ltd., Osaka, Japan

[21] Appl. No.: 191,183

[22] Filed: May 6, 1988

[30] Foreign Application Priority Data

Jun. 4, 1987 [JP] Japan .................. 62-138898
Aug. 27, 1987 [JP] Japan .................. 62-211448

[51] Int. Cl.⁵ .................. A61K 9/00
[52] U.S. Cl. .................. 424/400; 424/422; 424/451; 424/456; 424/464; 424/478; 424/479; 424/480; 424/499; 424/501; 514/512; 514/518; 514/535; 514/554; 514/557; 514/561; 514/562; 514/563; 514/880; 560/12; 560/17; 560/19; 560/45; 562/455
[58] Field of Search .................. 424/400, 422, 451, 456, 424/464, 478, 479, 480, 499, 501; 514/512, 518, 535, 554, 557, 880, 561, 562, 563; 562/455; 560/12, 17, 19, 45

[56] References Cited

U.S. PATENT DOCUMENTS 3,549,689 12/1970 Frey et al. .................. 562/455
4,317,817 3/1982 Blohm et al. .................. 514/150
4,395,615 8/1983 Petrow et al. .................. 514/177
4,396,615 8/1983 Petrow et al. .................. 514/177
4,684,635 8/1987 Orentreich et al. .................. 514/170
4,737,362 4/1988 Yoshizumi et al. .................. 514/852 X Primary Examiner—Thurman K. Page
Attorney, Agent, or Firm—Stevens, Davis, Miller & Mosher

[57] ABSTRACT

A benzoylaminophenoxybutanoic acid derivative of general formula:

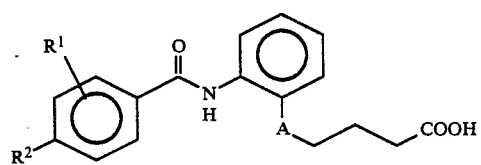

(I)

[wherein
A represents oxygen atom, sulfur atom or sulfinyl (SO) group,
$R^1$ represents hydrogen atom or methyl group,
$R^2$ represents a group of the general formula:

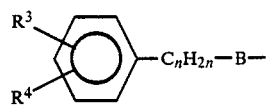

(i)

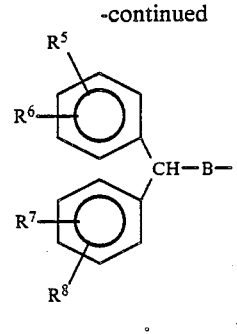

(ii)

or

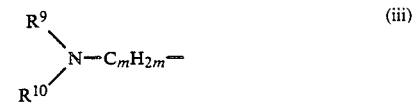

(iii)

{wherein
B represents oxygen atom, sulfur atom or a group of general formula: NR″ (wherein R″ represents hydrogen atom or alkyl group of from 1 to 4 carbon atoms(s)), $R^3$, $R^4$, $R^5$, $R^6$, $R^7$ and $R^8$ represent, independently, hydrogen atom, alkyl group of from 1 to 4 carbon atom(s), halogen atom or trifluoromethyl group,
m represents 0 or 1,
n represents an integer of from 1 to 4, and
$R^9$ and $R^{10}$ represent, independently, hydrogen atom, alkyl group of from 1 to 5 carbon atom(s) or a group of general formula:

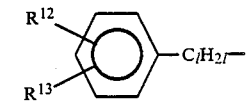

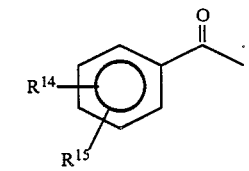

or

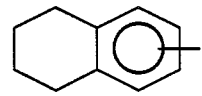

(wherein $R^{12}$, $R^{13}$, $R^{14}$ and $R^{15}$ represent, independently, hydrogen atom, alkyl group of from 1 to 4 carbon atom(s), halogen atom or trifluoromethyl group, and l represents an integer of from 1 to 4.).

With the proviso that $R^9$ and $R^{10}$ do not represent hydrogen atoms at the same time.}.] or non-toxic salts thereof possess an inhibitory activity on 5α-reductase, and therefore be useful for treating and/or preventing agent for alopecia, acnes or prostatic hypertrophy.

19 Claims, No Drawings

BENZOYLAMINOPHENOXYBUTANOIC ACID DERIVATIVES

DESCRIPTION

Summary

This invention is related to novel benzoylaminophenoxybutanoic acid derivatives having an inhibitory activity on 5α-reductase of the following general formula (I):

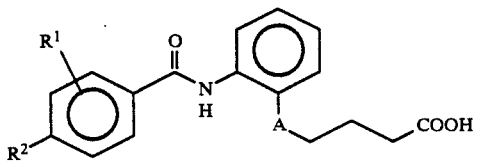

[wherein all of the symbols are the same meaning as hereafter defined.]

Purpose of the Invention

Purpose of the present invention is to provide the novel compounds being unknown up to now. These compounds are useful for the treatment and/or prevention of diseases (alopecia, pimple prostatauxe etc.) that result from excess production of dihydroteststerone.

Background

So far, many theories are exposited such as (1) imbalance of hormones, (2) genetics, (3) circulatory failure, (4) nutrition, as the origin of androgenic alopecia.

And it has been also suggested that testosterone (androgenic hormone) played an important role on the generation of hairs from old.

The theory of Adachi at al in which the relation between testosterone and androgenic alopecia is proved by biochemical experiments, is as follows:

(i) first, testosterone biosynthesized in testis is converted into dihydrotestosterone by 5α-reductase existed in hair follicle, sebaceous gland etc. at head.
(ii) dihydrotestosterone reduces the activities of adenyl cyclase remarkably.
(iii) it decreases cyclic-AMP in cells.
(iv) last, it induces lowering of energy generation of hairs and limbus and supressing of protein synthesis (See Biochem. Biophys. Res. Commun., 41, 884 (1970)).

According to the theory it is thought that the series of the hairs in the growing phase shift to the resting phase, at the results of phenomena, the terminal hairs change to the soft hairs, and the androgenic alopecia.

A report by H. V. Schweikert supports this theory develops in the end that large quantities of metabolites by 5α-reductase such as dihydro testosterone etc. in hair follicles of androgenic alopecia patient exist more than that in females or healthy male.
(See J. Clin. Endocr., 38, 811 (1974))

It was reported that dihydrotestosterone converted from testosterone by 5α-reductase also plays in an important physiological role in the generate of acnes (acne, pimple etc.) other than androgenic alopecia. J. B. Hay et al reported that the metabolism of testosterone by 5α-reductase was enhanced in the affected part of acne aggravated, from the study in the flux between affected skin of acne-patient and healthy skin (See Br. J. Dermatol., 91, 123 (1974)).

G. Sansone et al found that synthetic ability of dihydrotestosterone from testosterone developed from two to twenty times in the affected part of acne-patient compared to that in healthy man, and they suggested that dihydrotestosterone generated by 5α-reductase greatly relates to the generation or aggravation of acne (See J. Invest. dermatol., 56, 366 (1971)).

And, dihydrotestosterone is related to the hypertrophy of prostate. Cowan et al reported that much dihydrotestosterone existed in the prostate of prostatic hypertrophy-patient (See J. Steroid Biochemistry, 11, 609 (1979)). Recently, it was known that activity of 5α-reductase in prostate of prostatic hypertrophy-patient aggravated abnormally (See J. Clinical Endocrinol and Metabolism, 56, 139 (1983)).

From those informations it has been clear that dihydrotestosterone plays an important role in the generation and development of prostatic hypertrophy.

PRIOR ARTS AND COMPARISON WITH THEM

On the above background, recently, researches and developments of 5α-reductase inhibitors are carried out energetically and they are mainly steroids or derivatives thereof.

Widespread investigation has been carried out in order to discover compound which have a non-steroid structure, and possess inhibitory activity on 5α-reductase. The present applicant have found that the above purpose can be accomplished by compounds wherein cinnamic acid or benzoic acids form amides with anilines, and then applicated the patents

[See
1 Japanese Patent Kokai No. 60-97946,
2 Japanese Patent Kokai No. 60-116657,
3 Japanese Patent Kokai No. 60-142936,
4 Japanese Patent Kokai No. 60-142941,
5 Japanese Patent Kokai No. 60-146855,
6 Japanese Patent Kokai No. 61-126061, i.e, the European Patent Publication No. 173516,
7 Japanese Patent Kokai No. 62-198652 and
8 Japanese Patent Kokai No. 62-198653.]

In the application 6 among the above applications, it is disclosed that a series of compounds of the general formula (extracted partially):

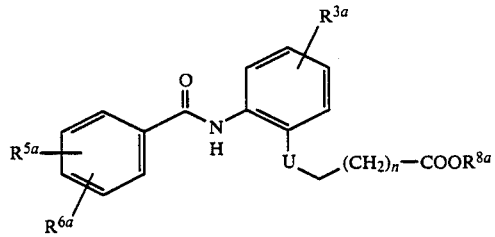

[wherein
$R^{3a}$ represents hydrogen atom, halogen atom etc., $R^{5a}$ and $R^{6a}$ represent independently, hydrogen atom or halogen atom, or straight or branched chain alkyl, alkenyl or alkynyl group of from 1 to 20 carbon atom(s) which may be replced optional one, two, three, four or five carbon atom(s) by oxygen atom, sulfur atom, halogen atom, nitrogen atom, benzene ring, thiophene ring, naphthalene ring, carbocyclic ring of from 4 to 7 carbon atoms, carbonyl group, carbonyloxy group, hydroxy group, carboxy group, azido group, nitro group, $R^{8a}$ represents hydrogen atom or straight or branched chain alkyl group of from 1 to 6 carbon atom(s), U represents oxygen atom or sulfur atom, and n represents an integer of from 1 to 10.] possess an inhibitory activity on 5α-reductase, antagonistic activity on SRS, inhibitory activity on aldose reductase and inhibitory activity on phospholipase.

The present inventors synthesized novel compounds, which were included to claim of the above invention and were not disclosed specifically.

And they found that these compounds possess unexpected strong inhibitory activity on 5α-reductase, having completed the present invention.

Further, several compounds similar to the compounds of the present invention in structure, are known, e.g.

9 British Pat. No. 1077936,
10 British Pat. No. 1088295,
11 U.S. Pat. No. 3549689
12 PCT Patent Publication No. 8605779.

But the purpose of these applications are invention of compounds having anti-inflammatory activity (including antagonistic activity of SRS), and therefore, are different from the purpose of the present invention i.e. to invent compounds having inhibitory activity on 5α-reductase.

In the structure and purpose, compounds of applications 9, 10 and 11 are different from the compounds of the present invention.

Patent publication 12 disclose compounds of the following general formula (partial extraction):

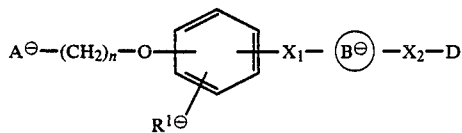

[wherein $A^e$ represents hydrogen atom, phenyl or phenoxy group, n represents 3–10, $R^{1e}$ represents hydrogen atom or lower alkoxy group, $X^1$ represents —CONH— etc., $B^e$ represents

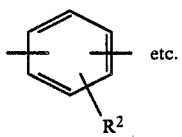 etc.

(wherein $R^2$ represents hydrogen atom, halogen atom, nitro group etc.) $X^2$ represents —O—$Y^4$— etc. (Wherein $Y^4$ represents alkylene group of from 1 to 6 carbon atom(s) etc.), and D represents carboxy group, alkoxycarbonyl group etc.], having antagonistic activity of SRS. The scope of the above invention and that of the present invention overlap each other. However, there is no compounds specifically disclosed in overlap. And further the purpose of patent publication 12 is different from that of the present invention.

It has been confirmed by our experiment that an inhibitory activity on a 5α-reductase, of compound having the chemical structure similar to the compounds of the present invention is very weak. The fact does not suggest strong inhibitory activity on 5α-reductase of compounds in the present invention.

DISCLOSURE OF THE INVENTION

As mentioned-above, the present invention is the selective invention of the invention described in Japanese Patent Kokai No. 61-126061 i.e. the European Patent Publication No. 173516.

The present invention is related to (1) benzoylaminophenoxybutanoic acid derivatives of the general formula:

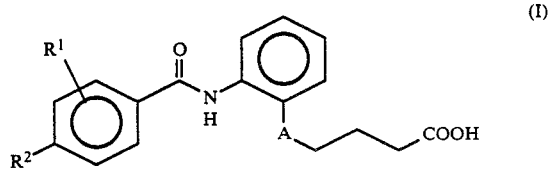

[wherein

A represents oxygen atom, sulfur atom or sulfinyl (SO) group, $R^1$ represents hydrogen atom or methyl group, $R^2$ represents a group of the general formula:

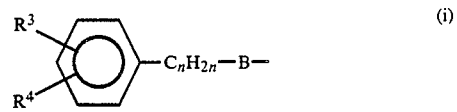

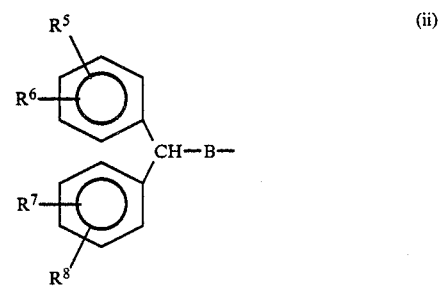

or

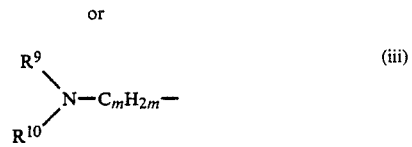

{in the each formula,

B represents oxygen atom, sulfur atom or a group of general formula: NR″ (wherein R″ represents hydrogen atom or alkyl group of from 1 to 4 carbon atom(s)), $R^3$, $R^4$, $R^5$, $R^6$, $R^7$ and $R^8$ represent, independently, hydrogen atom, alkyl group of from 1 to 4 carbon atom(s), halogen atom or trifluoromethyl group, m represents 0 or 1, n represents an integer of from 1 to 4, and $R^9$ and $R^{10}$ represent, independently, hydrogen atom, alkyl group of from 1 to 5 carbon atom(s) or a group of general formula:

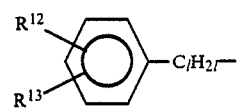

-continued

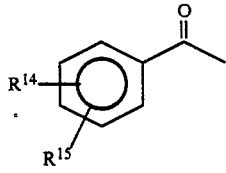

or

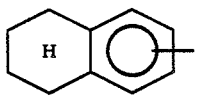

(wherein $R^{12}$, $R^{13}$, $R^{14}$ and $R^{15}$ represent, independently, hydrogen atom, alkyl group of from 1 to 4 carbon atom(s), halogen atom or trifluoromethyl group, and l represents an integer of from 1 to 4.). With the proviso that $R^9$ and $R^{10}$ do not represent hydrogen atoms at the same time.}.] or non-toxic salts thereof, and (2) inhibitory agent on 5α-reductase containing them as active ingredient.

In the general formula (I), alkyl group of from 1 to 4 carbon atom(s) represented by $R^3$, $R^4$, $R^5$, $R^6$, $R^7$, $R^8$, $R^{11}$, $R^{12}$, $R^{13}$, $R^{14}$ and $R^{15}$ means methyl, ethyl, propyl and butyl groups and isomeric groups (contains branched-chain) thereof.

In the general formula (I), alkyl group of from 1 to 5 carbon atom(s) represented by $R^{11}$ means groups described above and pentyl group and isomeric groups (contains branched-chain) thereof.

In the general formula (I), halogen atom represented by $R^3$, $R^4$, $R^5$, $R^6$, $R^7$, $R^8$, $R^{12}$, $R^{13}$, $R^{14}$ and $R^{15}$ means fluorine atom, chlorine atom, bromine atom and iodine atom.

The present invention can be separated three groups of compounds by the kind of $R^2$.

That is, it can be classified by the groups of compounds represented by the general formula:

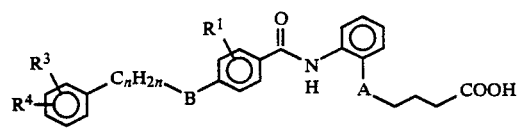
(I-i)

and

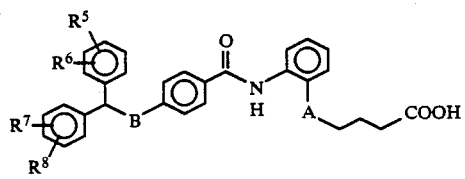
(I-ii)

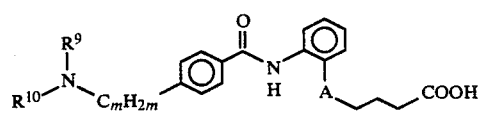
(I-iii)

[in the each formula, all symbols are the same meaning as defined hereinbefore.]

Salts

The compounds of the general formula (I) may be converted into the corresponding salts by known method. Non-toxic and water-soluble salts are preferable. Suitable salts, for example, are follows: salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, penethylamine, piperidine, monoethanolamine, diethanolamine, tris(hydroxymethyl)aminomethane, lysine, arginine, N-methyl-D-glucamine etc.).

Process for the preparation

Among the compounds of the present invention of the general formula (I), compounds wherein A is oxygen atom, sulfur atom or a group of general formula: $NR^{11}$ (wherein $R^{11}$ is the same meaning as defined hereinbefore.), i.e. the compounds of the general formula:

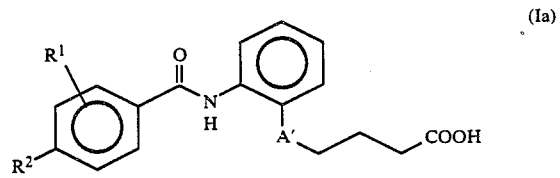
(Ia)

[wherein A' represents oxygen atom, sulfur atom or a group of general formula:
$NR^{11}$ (wherein $R^{11}$ is the same meaning as defined hereinbefore.), and other symbols are the same meaning as defined hereinbefore.] may be subjected to hydrolysis (saponification; described hereinafter) of the compound of the general formula:

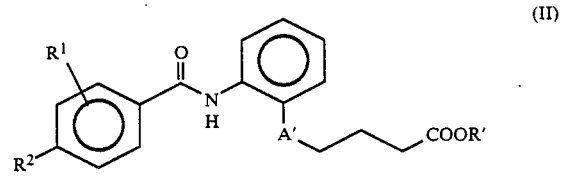
(II)

Conversion of an ester into corresponding acid (saponification) is known, and it may be carried out, for example, using an aqueous solution of alkali (lithium hydroxide, potassium hydroxide, sodium hydroxide, potassium carbonate, sodium carbonate etc.) in a water-miscible organic solvent (dimethoxyethane, THF, dioxane, ethanol, methanol etc.). The reaction is carried out at a temperature of from −10° C. to 100° C.

Among the compounds of the general formula (I), the compounds wherein A is sulfinyl group can be prepared by oxidizing the compounds wherein A is sulfur atom.

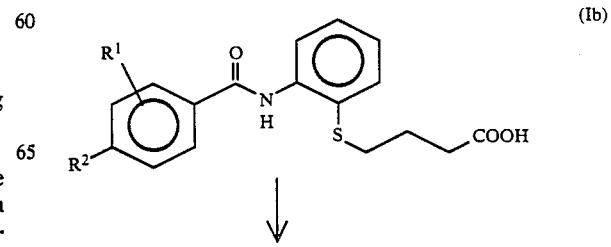
(Ib)

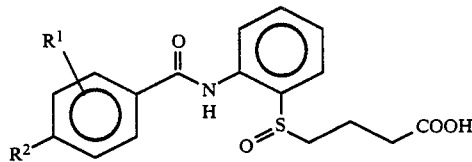
(Ic)

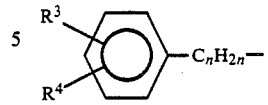

[in the each formula, all symbols are the same meaning as defined hereinbefore.]

The oxidation is known, and it may be carried out, for example, using an aqueous solution of perhalogenate (meta-sodium periodate etc.), in a water-miscible organic solvent (methanol, ethanol, dimethoxyethane etc.).

The compounds of the general formula (II) can be prepared by the following reaction scheme (A).

Every reaction in the scheme is known and each symbol represents the following meanings or as defined hereinbefore, respectively.

R — group of the general formula:

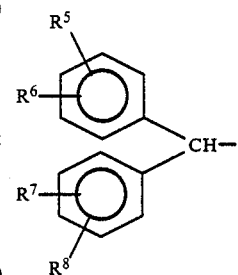

$X^1$, $X^2$, $X^3$, $X^4$, $X^5$ — halogen atom, tosyl group or mesyl group.

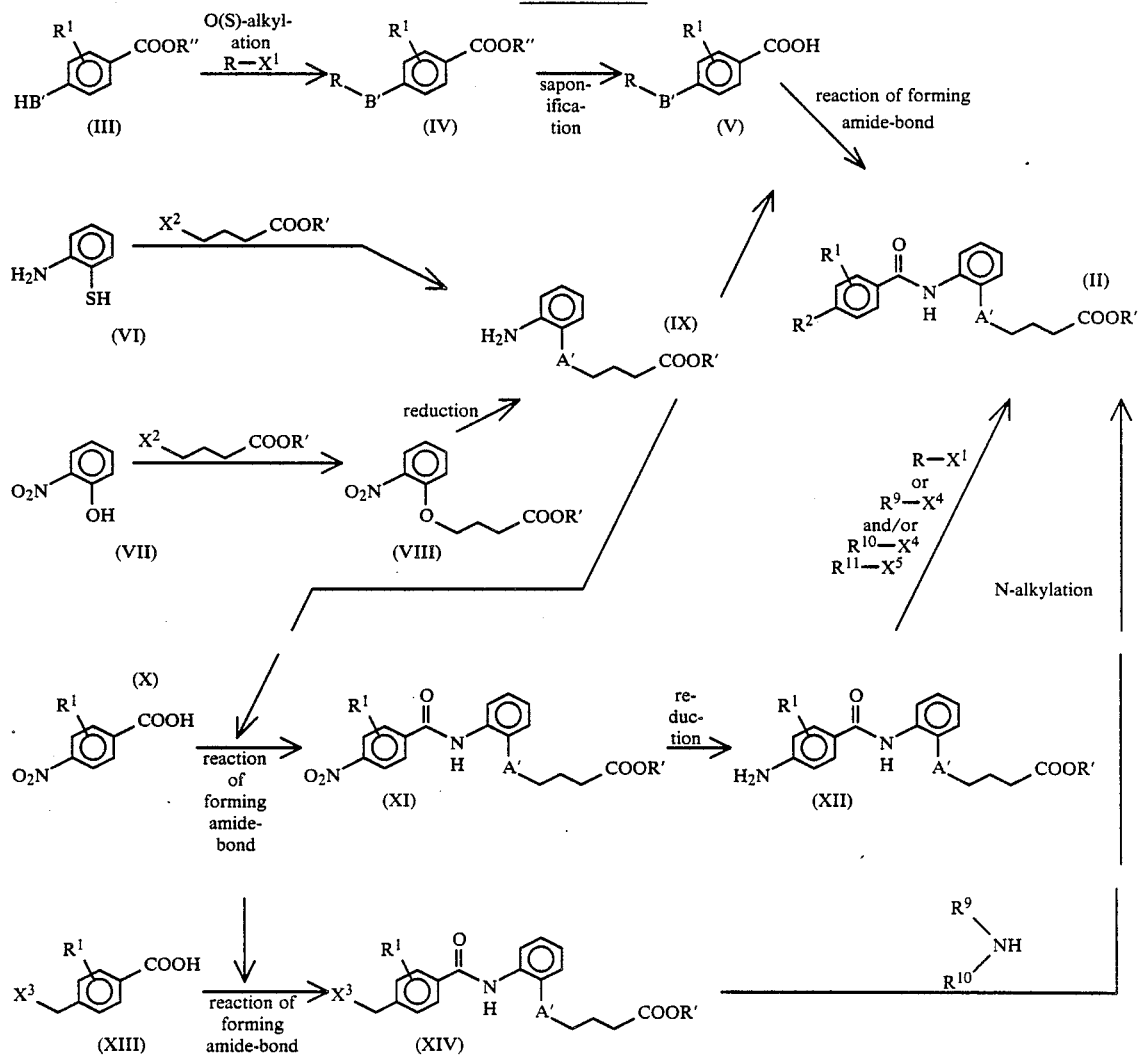

A' — oxygen atom or sulfur atom.
B' — oxygen atom or sulfur atom.
R'' — alkyl group of from 1 to 4 carbon atom(s).

Reaction products may be purified by conventional methods, for example, distillation at atmospheric or reduced pressure, high performance liquid chromatography, thin layer chromatography or column chromatography using silica gel or magnesium silicate or washing or recrystallization. Purification may be carried out between each reactions or after a series of reactions.

Starting materials

Starting materials and reagents in the present invention are known per se or may be prepared by known methods.

Pharmacological Activities

The compounds of the present invention of the general formula (I) possess an inhibitory activity on 5α-reductase, described before, for example, in a standard laboratory test, the following results are given.

5α-reductase inhibitory activity in vitro

The compounds of the present invention showed activities as in the following Table I, with the test system described hereafter.

TABLE 5

| α-reductase inhibitory activity | | | |
|---|---|---|---|
| Example No. of the compound | IC$_{50}$ (μM) | Example No. of the compound | IC$_{50}$ (μM) |
| 1 | 0.08 | 2(i) | 0.15 |
| 1(a) | 0.2 | 2(j) | 0.026 |
| 1(b) | 0.33 | 2(k) | 0.58 |
| 1(c) | 0.32 | 2(l) | 0.15 |
| 1(d) | 0.13 | 2(m) | 0.12 |
| 1(e) | 0.22 | 2(n) | 0.04 |
| 1(f) | 0.2 | 2(o) | 0.035 |
| 1(g) | 0.44 | 2(p) | 0.08 |
| 1(h) | 0.57 | 2(q) | 0.22 |
| 1(i) | 0.43 | 2(r) | 0.0025 |
| 2 | 0.011 | 2(s) | 0.011 |
| 2(a) | 0.023 | 3(a) | 0.056 |
| 2(b) | 0.025 | 3(b) | 0.025 |
| 2(c) | 0.3 | 4(a) | 0.0030 |
| 2(d) | 0.025 | 4(b) | 0.0065 |
| 2(e) | 0.044 | 5 | 0.065 |
| 2(f) | 0.17 | 6(a) | 0.3 |
| 2(g) | 0.027 | 6(b) | 0.23 |
| 2(h) | 0.14 | 6(c) | 0.14 |

Compared compound ① :    2~5
Compounds group disclosed specifically in the specification of the European Patent Publication No. 173516 and have measured inhibitory activity on 5α-reductase practically
Compared compound ② :    >20

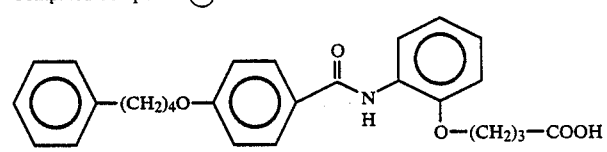

(the compound of example No. 92 in the specification of PCT Patent Publication No. 8605779)

It is obvious from Table I that all compounds of the present invention possess strong inhibitory activity on 5α-reductase.

An inhibitory activity on 5α-reductase of the compound of the present invention is approximately 10 to $10^3$ times as strong as that of compared compounds ①, ', and further that of the present invention is far stronger than that of the compared compound ②.

It is quite unexpected that such strong compounds exist within the scope of the patent application (Japanese Patent Kokai No. 61-126061 i.e. the European Patent Publication No. 173516) including the compared compound.

The above experiment was carried out in vitro. On the other hand, it is known that the compound wherein $R^1$ is a methyl group in the general formula (I) of the present invention is stable for the enzyme in liver, and therefore, those compounds are more useful as practical medicine.

Inhibitory activity on 5α-reductase in vitro was measured by the following test system.

The test was carried out by being referred to the method of J. Shimazaki et al [See Endocrinol, Japan., 18, 179 (1971)].

Male rats' prostate (4g) was homogenized with its 3-fold volume of 0.1 M HEPES buffer (pH 7.4) including 0.25 M cane sugar, and was centrifuged at 3000 r.p.m. for 10 mins.

The precipitate was suspended into the buffer solution described above (10 ml), and the suspension was centrifuged at 3000 r.p.m. for 5 mins. The resulting precipitated was suspended in the buffer solution (3 ml) described above and was used as a sauce of enzyme.

A reaction mixture (total volume 0.1 ml) of [4-$c^{14}$]testosterone (1.5n mol, 1.5×10$^5$ cpm), NADPH (0.5 μmol), enzyme solution (0.03 ml) described above and several kinds of concentration of the compounds in the present invention was incubated for 60 mins at 37° C. Enzyme reaction was quenched by addition of a mixture (0.4 ml) of chloroform and methanol (1:2), and the mixture was centrifuged at 2000 r.p.m. for 3 mins. The supernatant (50 μl) was spotted on silica gel thin layer plate. The spot on the plate was developed with a mixture of chloroform, methanol and acetic acid (99.2:0.6:0.2). Radioactivity of dihydrotestosterone generated on the plate was measured by TLC scanner of radio-autography and inhibitory ratio was calculated.

Toxicity

On the other hand, it was confirmed that the toxicity of the compounds of the present invention was very low. Therefore, the compounds of the present invention may be considered to be sufficiently safe and suitable for pharmaceutical used.

Application for the Pharmaceuticals

To inhibit 5α-reductase is to prevent the excess generation of dihydrotestosterone, described before, and therefore be useful for prevention and/or treatment for alopecia such as male type alopecia, acen and prostatic hypertrophy in animals including human beings, especially human beings.

The compounds of the present invention possess a inhibitory activity on 5α-reductase in vitro, so it is expected to be useful for prevention and/or treatment of alopecia such as male type alopecia, acne and prostatic hypertrophy.

For the purpose above described, the compounds of the present invention may normally be administered systemically (mainly in the case of prevention and/or treatment prostatic hypertrophy) or partially (mainly in the case of prevention and/or treatment of a alopecia and acne), usually by oral or parenteral administration.

The doses to be administered are determined depending upon age, body weight, symptom, the desired therapeutic effect, the route o administration, and the duration of the treatment etc. In the human adult, for the treatment and/or prevention of prostatic hypertrophy, the doses per person per dose are generally between 1 mg and 1 g, by oral administration, up to several times per day, and between 100 µg and 100 mg, by parenteral administration (preferably intravenous administration) up to several times per day.

In the human adult, for the treatment and/or prevention of alopecia and/or acne, the doses per person per dose are generally between 10 µg and 50 mg, by dermal administration up to several times per day.

As mentioned above, the doses to be used depend upon various conditions. Therefore, there are cases in which doses lower than or greater than the ranges specified above may be used.

In the administration, the compounds of the present invention was administered as solid compositions, liquid compositions and other compositions for oral administration and injections, external compositions and suppositories etc. for parenteral administration.

Solid compositions for oral administration, include compressed tablets, dispersible powders and granules etc. In such compositions, one or more of the active compound(s) is or are, admixed with at least done inert diluent (lactose, mannitol, glucose, hydroxypropylcellulose, microcrystalline cellulose, starch, polyvinylpyrrolidone, magnesium metasilicate alminate etc.). The compositions may also comprise, as is normal practice, additional substances other than inert diluents: e.g. lubricating agents (magnesium stearate etc.), disintergrating agents (cellulose calcium gluconate etc.), stabilizing agent (lactose etc.) and assisting agent for dissolving (glutamic acid, aspertic acid etc.).

The tablets or pills may, if desired, be coated with gastric or enteric material (sugar, gelatin, hydroxypropylcellulose or hydroxypropylmethyl cellulose phthalate etc.).

Capsules include soft ones and hard ones.

Liquid compositions for oral administration include pharmaceutically-acceptable emulsions, solutions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agents etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride sodium citrate, citric acid etc.).

For preparation of such spray compositions, for example, the method described in the U.S. Pat. No. 2868691 or 3095355 may be used.

Injections for parenteral administration include sterile aqueous or non-aqueous solutions, suspensions and emulsions. In such compositions, one or more of active compound(s) is or are admixed at least one of inert aqueous diluent(s) (distilled water for injection, physiological salt solution etc.) or inert non-aqueous diluent(s) (propylene glycol, polyethylene glycol, olive oil, alcohols such as ethanol, POLYSOLBATE 80 (registered trade mark) etc.).

Injections may comprise additional other than inert diluents: e.g. preserving agents, wetting agents, emulsifying agents, dispersing agents, stabilizing agents (lactose etc.), assisting agents such as assisting agents for dissolving (glutamic acid, aspertic acid etc.).

They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before used.

Other compositions for parenteral administration include liquids for external use, endermic liniments (ointment etc.), suppositories as intra-rectal administration which comprise one or more of the active compound(s) and may be prepared by known methods.

Compositions for dermal administration, especially for the treatment and prevention of alopecia and acne, include liquids for external use such as lotion, tonic, spray, solution, suspension, emulsion and liniments such as ointment, gel, cream.

Such compositions may comprise one or more of active ingredient(s) and at least one of inert diluent(s), for example, distilled water, lower alcohols such as ethanol, higher alcohols such as cetanol, poly alcohols such as polyethylene glycol, propylene glycol, celluloses such as hydroxypropyl cellulose, animal or plant fats, vaseline, wax, silicone, plant oil such as olive oil, surfactants, zinc oxide etc.

Besides inert diluents, such composition may also comprise adjuvants (wetting agents, suspending agent, perfuming agents, preserving agents).

Reference examples and Examples

The following reference examples and examples illustrate the present invention, but not limit the present invention.

Unless otherwise specified, "IR" were measured KBr tablet method.

REFERENCE EXAMPLE 1

Synthesis of 4-(2-nitrophenoxy)butanoic acid ethyl ester

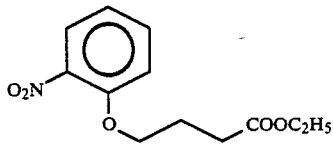

DMF solution (100 ml) of 0-nitrophenol (60 g) was added dropwise with stirring to DMF suspension (500 ml) of sodium hydride (16.5 g; 62%) cooled with ice.

Further, the mixture was stirred for 1 hour at room temperature, and further DMF solution (200 ml) of 4-bromobutanoic acid ethyl ester (84.2 g) was added to the reaction mixture.

The reaction solution was stirred for 15 hours at 70° C., and evaporated.

Ethyl acetate ($E_tOA_c$) was added to the residue, and the mixture was washed with successive, water and a saturated aqueous solution of sodium chloride, dried and evaporated.

The residue was purified by column chromatography on silica gel ($E_tOA_c$:hexane=1:3) to give the title compound (77.3 g) having the following physical data.

TLC:Rf 0.35 ($E_tOA_c$:hexane=1:2).

REFERENCE EXAMPLE 2

Synthesis of 4-(2-aminophenoxy) butanoic acid ethyl ester

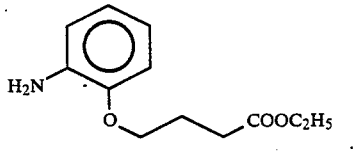

Under an atmosphere of hydrogen, ethanol solution (500 ml) of the compound (77 g) prepared in reference example 1 was added to the suspension of chloroform (100 ml) and ethanol (500 ml) of paradium-carbon (13.1 g; 10%), and the mixture was stirred for 10 hours at room temperature.

The reaction mixture was filtered off, and the filtrate was evaporated.

The saturated aqueous solution of sodium bicarbonate (500 ml) was added to ehyl acetate (1000 ml) of the residue, the mixture was stirred at room temperature.

The organic layer was washed with a saturated aqueous solution of sodium chloride, dried and evaporated.

The residue was purified by column chromatography on silica gel (hexane:$E_tOA_c$:$CH_2Cl_2$=70:15:15) to give the title compound (60 g) having the following physical data.

TLC:Rf 0.43 (hexane:$E_tOA_c$:$CH_2Cl_2$=2:1:1).

REFERENCE EXAMPLE 3

Synthesis of 4-isobutylbenzyl bromide

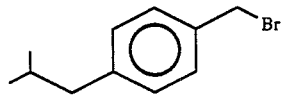

Carbon tetrachloride solution (15 ml) of 4-isobutylbenzyl alcohol (3.58 g) was added to carbon tetrachloride solution (30 ml) of tribromophosphine (10.3 g) with stirring at room temperature.

The reaction mixture was refluxed for two hours and cooled at room temperature.

The reaction solution was poured into ice-cold water, and ethyl acetate was added to the solution.

The organic layer was washed with a saturated aqueous solution of sodium chloride, dried and evaporated.

The residue was purified by column chromatography on silica gel ($E_tOA_c$:hexane=1:4) to give the title compound (4.47 g) having the following physical data.

TLC:Rf 0.89 ($E_tOA_c$:hexane=1:4).

REFERENCE EXAMPLE 4

Synthesis of 4-(4-isobutylphenylmethoxy) benzoic acid

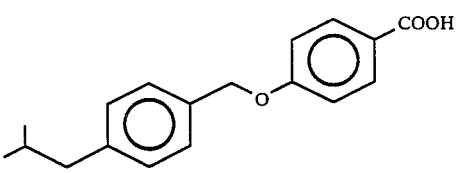

Under an atmosphere of argon, DMF solution (5 ml) of 4-hydroxybenzoic acid methyl ester (1.67 g) was added dropwise to DMF suspension (30 ml) of sodium hydride (423 mg; 62%) at room temperature, and the mixture stirred for 10 minutes.

DMF solution (5 ml) of the compound (2.26 g) prepared in reference example 3 was added to the reaction solution, and the mixture was stirred for 15 minutes at room temperature.

The reaction mixture was diluted with ether, washed with successive, water and a saturated aqueous solution of sodium chloride, dried and evaporated.

The residue was washed with small amount of hexane, and dissolved in mixture of THF (6 ml) and methanol (18 ml).

The two normal of aqueous solution of sodium hydroxide was added to the mixture solution, and the mixture was stirred for one and a half hours at room temperature.

The reaction solution was made acid with one normal of HCl, and prepared solution was extracted with ethyl acetate.

The organic layer was washed with a saturated aqueous solution of sodium chloride, dried and evaporated to give the title compound (2.15 g) having the following physical data.

TLC:Rf 0.28 ($E_tOA_c$:hexane=1:1).

REFERENCE EXAMPLE 5

Synthesis of 4-[2-[4-(4-isobutylphenylmethoxy)benzolyamino]phenoxy butanoic acid ethylester

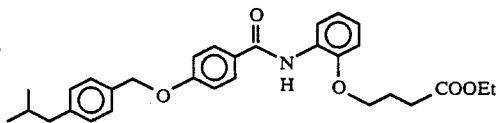

Thionyl chloride (4 ml) was added dropwise to methylene chloride solution (2 ml) of 4-(4-isobutylphenylmethoxy)benzoic acid (227 mg), and the mixture was refluxed for 1 hour and then evaporated.

Under an atmosphere of argon, the mixture solution of methylene chloride (5 ml) and pyridine (0.5 ml) of 4-(2-aminophenoxy) butanoic acid ethylester (179 mg) was cooled in an ice-bath, and an acid chloride thus obtained was added dropwise to this cooled solution.

After the solution was stirred for 10 minutes, the reaction solution was diluted with ethyl acetate.

The dilute solution was washed with successive, 1N HCl and a saturated aqueous solution of sodium chloride, dried and evaporated.

The residue was purified by column chromatography on silica gel ($E_tOA_c$:hexane=1:4) to give the title compound (374 mg) having the following physical data.

TLC:Rf 0.61 ($E_tOAf_c$:hexane=1:1)

REFERENCE EXAMPLE 6

Synthesis of 4-[2-(2-methyl-4-nitrobenzoylamino)-phenoxy]butanoic acid ethyl ester

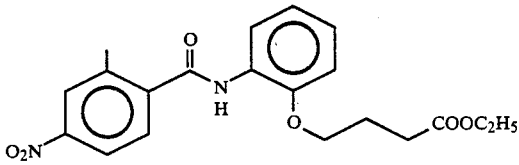

Thionylchloride (35 ml) was added to the solution of methylene chloride (35 ml) of 2-methyl-4-nitro benzoic acid (5.4 g), and the mixture was refluxed for one and a half hours.

The reaction was finished, and the reaction solution was concentrated.

The concentrate in methylene chloride (30 ml) was added dropwise to the mixture of amine (prepared in reference example 2; 7.31 g), pyridine (10 ml) and methylene chloride (60 ml) cooled with ice.

The reaction solution was stirred for 12 hours at room temperature, and evaporated.

Ethyl acetate was added to the residue, and the mixture was washed with successive water, dilute hydrochloride, water and a saturated aqueous solution of sodium chloride, dried and evaporated to give the title compound (11.0 g) having the following physical data.

TLC:Rf 0.83 (CHCl$_3$:$E_tOA_c$=10:1).

REFERENCE EXAMPLE 7

Synthesis of 4-[2-(4-amino-2-methylbenzoylamino)-phenoxy]butanoic acid ethyl ester

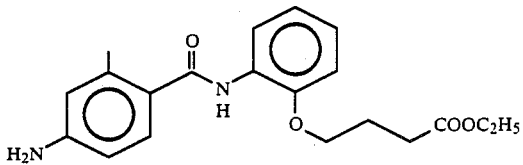

Ethanol (400 ml) and palladium-carbon (10%; 2 g) were added to nitro compound (20.2 g) prepared in reference example 6.

Under an atmosphere of hydrogen, the mixture was vigorously stirred for two and a half hours.

The reaction solution was filtered off, the filtrate was evaporated to give the title compound (18.37 g) having the following physical data.

TLC;Rf 0.28 (CHCl$_3$:$E_tOA_c$=10:1)

REFERENCE EXAMPLE 8

Synthesis of 4-[2-[2-methyl-4-[N,N-bis(4-propylbenzyl)amino]benzoylamino]phenoxy]butanoic acid ethyl ester

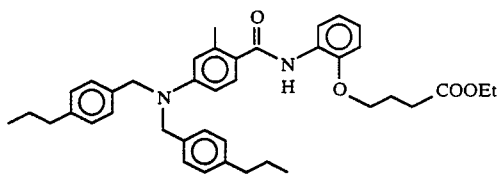

4-propylbenzyl bromide (318 mg) and sodium bicarbonate (150 mg) were added to the solution of isopropyl alcohol (5 ml) of amine (356 mg) prepared in reference example 7, and the mixture was stirred for one and a half hours at 70° C.

The reaction solution was evaporated, and the residue in ethyl acetate was washed with successive, water and a saturated aqueous solution of sodium chloride, and dried and evaporated.

The residue was purified by column chromatography on silica gel (hexane:$E_tOA_c$=4:1) to give the title compound having the following physical data.

TLC:Rf 0.79 (CHCl$_3$:$E_tOA_c$=10:1)

REFERENCE EXAMPLE 8(a)

Synthesis of 4-[2-[2-methyl-4-[N-(4-propylbenzyl)amino]benzoylamino]phenoxy]butanoic acid ethyl ester As a by-product in reference example 8, the title compound (137 mg) having the following physical data was given.

TLC:Rf 0.64 (CHCl$_3$:$E_tOA_c$=10:1).

REFERENCE EXAMPLE 9

Synthesis of 4-[2-(4-chloromethyl benzoylamino)-phenoxy]butanoic acid ethyl ester

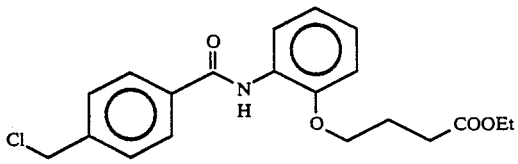

Thionyl chloride solution (6 ml) of p-chloromethyl benzoic acid (1.76 g) was refluxed for 1 hour, an excess of thionyl chloride was evaporated. Methylene chloride solution (10 ml) of acid chloride thus obtained was added dropwise to the mixture solution of pyridine (5 ml) and methylene chloride (20 ml) of 4-(2-aminophenoxy)butanoic acid ethyl ester cooled with ice, and the mixture was stirred for 2 hours at room temperature.

The reaction mixture was diluted with ethyl acetate, and the dilute solution was washed with successive, one normal HCl and a saturated aqueous solution of sodium chloride, dried and evaporated.

The residue was purified by column chromatography on silica gel (hexane:$E_tOA_c$=5:1) to give the title compound (3.38 g).

REFERENCE EXAMPLE 10

Synthesis of 4-[2-[4-(5,6,7,8-tetrahydronaphthalene-1-yl)amino methylbenzoylamino]phenoxy]butanoic acid ethyl ester

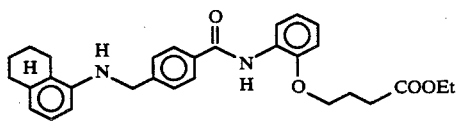

The mixture of the compound (770 mg; prepared in reference example 9), 1-amino-5,6,7,8-tetrahydronaphthalene (541 mg), potassium carbonate (276 mg) and DMF (6 ml) was stirred for 6 hours at 70° C.

Under cooling with ice, the reaction mixture was neutralized with one normal of HCl (4 ml), and the neutral solution was extracted with ethyl acetate.

The organic layer was washed with water, dried and evaporated.

The residue was purified by column chromatography on silica gel (hexane: $E_tOA_c$=4:1) to give the title compound (650 mg).

REFERENCE EXAMPLE 11

Synthesis of 4-[2-[4-[N-methyl-N-(5,6,7,8-tetrahydronaphthalene-1-yl)aminomethylbenzoylamino]-phenoxy]butanoic acid ethyl ester

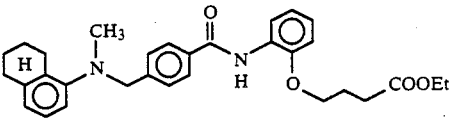

The mixture of the compound (393 mg; prepared in reference example 10), methyl iodide (574 mg) and DMF (4 ml) was stirred for 12 hours at room temperature.

The reaction solution was evaporated, and ethyl acetate and sodium bicarbonate were added to this concentrate, shaken and extracted.

The organic layer was evaporated, and the residue was purified by column chromatography on silica gel (hexane: $E_tOA_c$=4:1) to give the title compound (229 mg).

EXAMPLE 1

Synthesis of 4-[2-[4-(4-isobutylphenylmethoxy)benzoylamino]phenoxy]butanoic acid

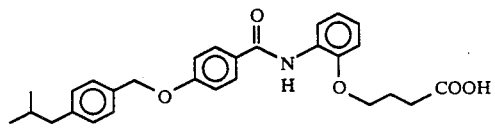

The aqueous solution of two-normal of sodium hydroxide (4 ml) was added to the mixture solution of THF (4 ml) and methanol (8 ml) of the compound (373 mg; prepared in reference example 3), and the mixture was stirred for 1 hour at room temperature.

The reaction solution was made acid with one normal of HCl, and prepared solution was extracted with ethyl acetate The organic layer was washed with a saturated aqueous of sodium chloride, dried and evaporated.

The residue was washed with hexane to give the title compound (255 mg) having the following physical data.
TLC: RF0.38 ($E_tOA_c$: hexane=2:1);
mp: 131°–134° C.

EXAMPLE 1(a)–1(i)

By the similar procedure as reference example from 1 to 3 and example 1, using a corresponding alcohol, compounds having the following physical data shown in the Table II, III and IV were given.

TABLE II

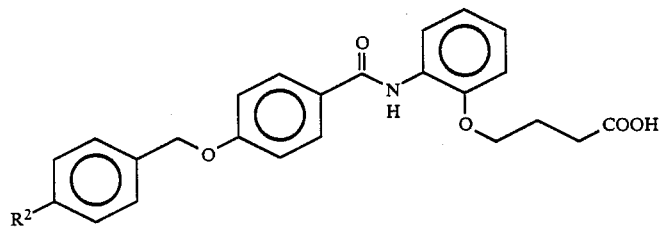

| Example No. | R²— | Name | TLC | MS |
|---|---|---|---|---|
| 1 (a) | H— | 4-[2-(4-benzyloxybenzoylamino) | Rf 0.61 | m/z 405, 231, |

TABLE II-continued

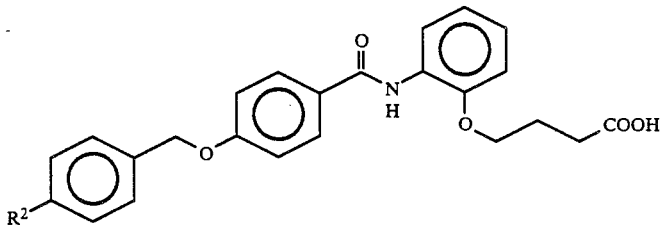

| Example No. | R²— | Name | TLC | | MS |
|---|---|---|---|---|---|
| | | phenoxy]butanoic acid | (EtOAc) | | 211 |
| 1 (b) | CH₃— | 4-[2-[4-(4-methylphenylmethoxy) benzoylamino]phenoxy] butanoic acid | Rf 0.21 (EtOAc:hexane = 1:1) | m/z | 419, 299, 225 |
| 1 (c) | C₂H₅— | 4-[2-[4-(4-ethylphenylmethoxy) benzoylamino]phenoxy] butanoic acid | Rf 0.27 (EtOAc:hexane = 1:1) | m/z | 433, 249, 119 |
| 1 (d) | CH₃—CH₂—CH₂— | 4-[2-[4-(4-propylphenylmethoxy) benzoylamino]phenoxy] butanoic acid | Rf 0.59 (EtOAc) | m/z | 447, 310, 253 |
| 1 (e) | (CH₃)₂CH— | 4-[2-[4-(4-isopropylphenylmethoxy) benzoylamino]phenoxy] butanoic acid | Rf 0.24 (EtOAc:hexane = 1:1) | m/z | 447, 361, 327, 287, 253 |

TABLE III

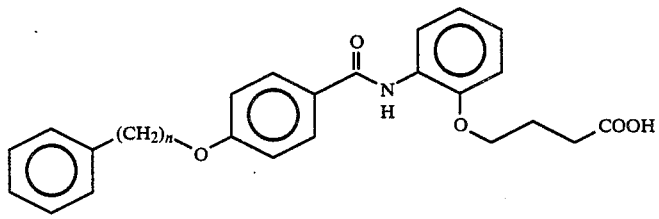

| Example No. | —(CH₂)ₙ— | Name | TLC | | MS |
|---|---|---|---|---|---|
| 1 (f) | —(CH₂)₃— | 4-[2-[4-(3-phenylpropoxy) benzoylamino]phenoxy] butanoic acid | Rf 0.22 (EtOAc) | m/z | 433, 347, 239 |
| 1 (g) | —(CH₂)₄— | 4-[2-[4-(4-phenylbutoxy) benzoylamino]phenoxy] butanoic acid | Rf 0.42 (EtOAc) | m/z | 447, 253 |

TABLE IV

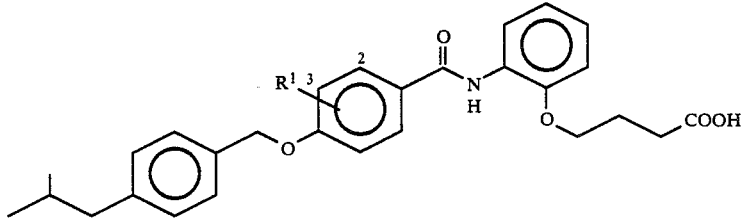

| Example No. | R²— | Name | TLC | mp |
|---|---|---|---|---|
| 1 (h) | 2-CH₃— | 4-[2-[4-(4-isobutyphenylmethoxy)-2-methylbenzoylamino]phenoxy] butanoic acid | Rf 0.32 (EtOAc:hexane = 1:1) | 125° C. |
| 1 (i) | 3-CH₃— | 4-[2-[4-(4-isobutyphenylmethoxy)-3-methylbenzoylamino]phenoxy] butanoic acid | Rf 0.29 (EtOAc:hexane = 1:1) | 113° C. |

EXAMPLE 2

Synthesis of 4-[2-[2-methyl-4-[N,N-bis(4-propylbenzyl)amino]benzoylamino]phenoxy]butanoic acid

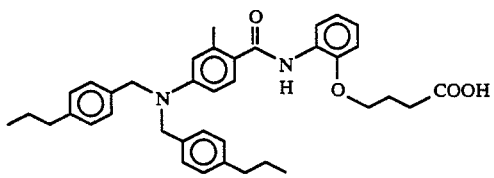

A one nomal of aqueous solution of lithium hydroxide (37 ml) was added to the solution of dimethoxyethane (70 ml) of ester (5.41 g; prepared in reference example 8), and the mixture was stirred for one and a half hours at 50° C., and evaporated.

Water was added to the residue, and the mixture was made acid with HCl to pH7, and the prepared solution was extracted with ethyl acetate.

The organic layer was washed with successive, water and a saturated aqueous solution of sodium chloride, dried and evaporated.

The residue was purified by recrystallization (hexane-$E_tOA_c$) to give the title compound (4.76 g) having the following physical data.

TLC: RF 0.58 ($E_tOA_c$: hexane=2:1);

IR: ν3320, 3200–2000, 1710, 1650, 1605, 1515, 1450 cm$^{-1}$.

EXAMPLE 2(a)–2(t)

By the similar procedure as reference example 6, 7 and 8 (or 8(a)) and example 2, compounds having the following physical data shown in the Table V and VI were given.

TABLE V

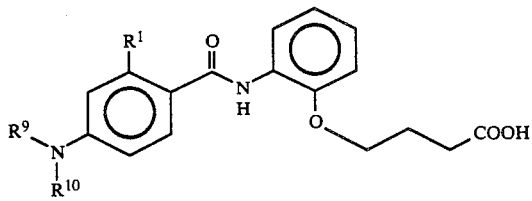

| Example No. | $R^9$, $R^{10}$, $R^1$ | Name | TLC | IR(cm$^{-1}$) or mp |
|---|---|---|---|---|
| 2 (a) | $R^9 = R^{10} =$ 4-propylbenzyl<br><br>$R^1 = H-$ | 4-[2-[4-[N, N-bis(4-propylbenzyl)amino]benzoylamino]phenoxy]butanoic acid | Rf 0.05 (EtOAc) | mp 121~122° C. |
| 2 (b) | $R^9 = R^{10} =$ 4-isobutylbenzyl<br><br>$R^1 = CH_3-$ | 4-[2-[4-[N, N-bis(4-isobutylbenzyl)amino]-2-methylbenzoylamino]phenoxy]butanoic acid | Rf 0.60 (hexane: EtOAc: = 1:1) | ν 3450, 3350, 2960, 2920, 2870, 1730, 1670, 1620, 1590, 1450, 1395, 1335, 1290, 1265 |
| 2 (c) | $R^9 = R^{10} =$ CH$_3$-pentyl<br><br>$R^1 = CH_3-$ | 4-[2-[4-[N, N-dipenthylamino)-2-methylbenzoylamino]phenoxy]butanoic acid | Rf 0.19 (hexane: EtOAc: = 2:1) | ν 3600~2300, 1730, 1620, 1610, 1530, 1450, 1340, 1260, 1220, 1050, 745 |
| 2 (d) | $R^9 = CH_3$-pentyl<br><br>$R^{10} =$ 4-propylbenzyl<br><br>$R^1 = CH_3-$ | 4-[2-[4-[N-penthyl-N-(4-propylbenzyl)amino]-2-methylbenzoylamino]phenoxy]butanoic acid | Rf 0.11 (hexane: EtOAc: = 2:1) | ν 3600~2300, 1705, 1640, 1600, 1510, 1440, 1330, 1250, 740 |
| 2 (e) | $R^9 = CH_3-$<br><br>$R^{10} =$ 4-propylbenzyl<br><br>$R^1 = CH_3-$ | 4-[2-[4-[N-methyl-N-(4-propylbenzyl)amino]-2-methylbenzoylamino]phenoxy]butanoic acid | Rf 0.11 (hexane: EtOAc = 1:1) | ν 3600~2200, 1700, 1650, 1605, 1510, 1440, 1325, 1260, 1210, 740 |

TABLE V-continued

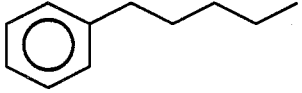

| Example No. | $R^9, R^{10}, R^1$ | Name | TLC | IR(cm$^{-1}$) or mp |
|---|---|---|---|---|
| 2 (f) | $R^9 = R^{10} =$ 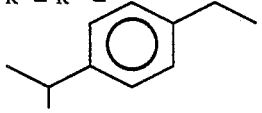 <br> $R^1 = CH_3-$ | 4-[2-[4-[N, N-bis(4-phenylbutyl)amino]-2-methylbenzoylamino]phenoxy]butanoic acid | Rf 0.51 (CH$_2$Cl$_2$: EtOAc: = 7:3) | ν 3600~2300, 1720, 1700, 1695, 1500, 1440, 1240, 1030, 740, 690 |
| 2 (g) | $R^9 = R^{10} =$ 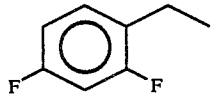 <br> $R^1 = CH_3-$ | 4-[2-[4-[N, N-bis(4-isopropylbenzyl)amino]-2-methylbenzoylamino]phenoxy]butanoic acid | Rf 0.78 (EtOAc) | ν 3470, 3350, 2980, 1730, 1670, 1605, 1515, 1450, 1400, 1290, 1260, 1240 |
| 2 (h) | $R^9 = R^{10} =$ 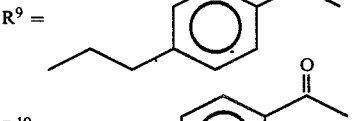 <br> $R^1 = CH_3-$ | 4-[2-[4-[N,N-bis-(2,4-difluorobenzyl)amino]-2-methylbenzoylamino]phenoxy]butanoic acid | Rf 0.76 (EtOAc) | mp 137~138° C. |
| 2 (i) | $R^9 =$ 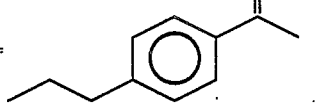 <br> $R^{10} =$ <br> $R^1 = CH_3-$ | 4-[2-[4-[N-(4-propylbenzyl)-N-(4-propylbenzoyl)amino]-2-methylbenzoylamino]phenoxy butanoic acid | Rf 0.26 (hexane: EtOAc = 1:1) | ν 3600-2300, 1720, 1650, 1600, 1515, 1450, 1250, 1115, 1040, 750 |
| 2 (j) | $R^9 = R^{10} =$ 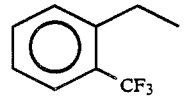 <br> $R^1 = CH_3-$ | 4-[2-[4-[N, N-bis(2-trifluoromethylbenzyl)amino]-2-methylbenzoylamino]phenoxy butanoic acid | Rf 0.66 (EtOAc: hexane = 2:1) | mp 148~149° C. |
| 2 (k) | $R^9 = R^{10} =$ 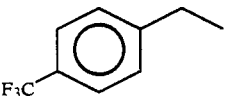 <br> $R^1 = CH_3-$ | 4-[2-[4-[N,N-bis-(4-trifluoromethylbenzyl)amino]-2-methylbenzoylamino]phenoxy]butanoic acid | Rf 0.68 (EtOAc: hexane = 1:1) | mp 165~166° C. |

TABLE VI

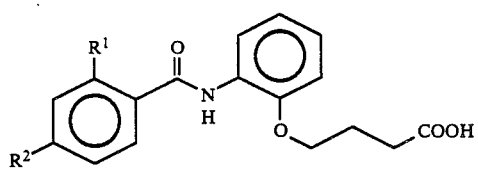

| Example No. | $R^2$, $R^1$ | Name | TLC | IR(cm$^{-1}$) or mp |
|---|---|---|---|---|
| 2 (l) | $R^2$ = (4-isobutylbenzyl)NH-CH$_2$-<br>$R^1$ = H— | 4-[2-[4-(4-isobutylbenzylamino) benzoylamino]phenoxy] butanoic acid | Rf 0.38 (EtOAc) | ν 3450–3350, 3300–2000, 1710, 1650, 1605, 1510, 1450, 1250, 760, 750 |
| 2 (m) | $R^2$ = (4-isobutylbenzyl)NH-CH$_2$-<br>$R^1$ = CH$_3$— | 4-[2-[4-(4-isobutylbenzylamino)-2-methylbenzoylamino]phenoxy] butanoic acid | Rf 0.39 (EtOAc: hexane: = 2:1) | ν 3450, 3350, 3000–2000, 1715, 1655, 1605, 1520, 1450, 1340 |
| 2 (n) | $R^2$ = (4-propylbenzyl)NH-CH$_2$-<br>$R^1$ = CH$_3$— | 4-[2-[4-(4-propylbenzylamino)-2-methylbenzoylamino]phenoxy] butanoic acid | Rf 0.35 (EtOAc: hexane: = 2:1) | ν 3450, 3350, 3100–2000, 1710, 1650, 1610, 1510, 1445, 1335, 1260 |
| 2 (o) | $R^2$ = (4-isobutylphenyl)ethylamino<br>$R^1$ = CH$_3$— | 4-[2-[4-[1-(4-isobutylphenyl) ethylamino]-2-methylbenzoylamino] pehnoxy]butanoic acid | Rf 0.13 (EtOAc: hexane: = 1:1) | ν 3600–2300, 1705, 1605, 1600, 1505, 1440, 1325, 1245, 1040, 840, 800, 750 |
| 2 (p) | $R^2$ = (4-isopropylbenzyl)NH-CH$_2$-<br>$R^1$ = CH$_3$— | 4-[2-[4-(4-isopropylbenzylamino)-2-methylbenzoylamino]phenoxy] butanoic acid | Rf 0.67 (EtOAc) | ν 3460, 3350, 2980, 1715, 1650, 1610, 1515, 1485, 1450, 1330, 1260 |
| 2 (q) | $R^2$ = (2-trifluoromethylbenzyl)NH-CH$_2$-<br>$R^1$ = CH$_3$— | 4-[2-[4-(2-trifluoromethylbenzylamino)-2-methylbenzoylamino]phenoxy] butanoic acid | Rf 0.44 (EtOAc: hexane: = 2:1) | mp 144–146° C. |
| 2 (r) | $R^2$ = bis(4-propylphenyl)methylamino<br>$R^1$ = CH$_3$— | 4-[2-[4-[bis(4-propylphenyl)methylamino]-2-methylbenzoylamino]phenoxy] butanoic acid | Rf 0.25 (EtOAc: hexane: = 1:1) | ν 3600–2300, 1705, 1600, 1505, 1445, 1330, 1250, 745 |

TABLE VI-continued

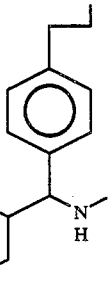

| Example No. | $R^2, R^1$ | Name | TLC | IR(cm$^{-1}$) or mp |
|---|---|---|---|---|
| 2 (s) | $R^2 =$ (bis(4-propylphenyl)methylamino group, NH); $R^1 = H-$ | 4-[2-[4-[bis(4-propylphenyl) methylamino]benzoylamino]phenoxy] butanoic acid | Rf 0.21 (EtOAc: hexane: = 1:1) | ν 3440~3300, 3300~2500, 2950, 2920, 2850, 1700, 1600, 1500, 1250, 760, 740 |
| 2 (t) | $R^2 =$ (bis(4-propylphenyl)methyl-N-methylamino group); $R^1 = H-$ | 4-[2-[4-[N-bis(4-propylphenylmethyl-N-methylamino] benzoylamino]phenoxy] butanoic acid | Rf 0.45 (EtOAc: hexane: = 1:1) | ν 3450, 3100-2300, 1705, 1600, 1505, 1440, 1245, 1190, 1100, 950, 755, 745 |

EXAMPLE 3(a)-3(b)

By the similar procedure as reference example 1, 6, 7, 8 and example 2, compounds having the following physical data shown in the Table VII were given.

EXAMPLE 4(a)-4(f)

By the similar procedure as reference example from 1 to 5 and example 1, compounds having the following physical data shown in the Table VIII were given.

TABLE VII

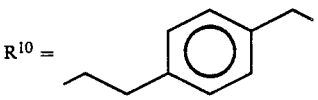

| Example No. | $R^9, R^{10}$ | Name | TLC | IR(cm$^{-1}$) or mp |
|---|---|---|---|---|
| 3 (a) | $R^9 = H-$; $R^{10} =$ 4-propylbenzyl | 4-[2-[4-(4-propylbenzylamino)-2-methylbenzoylamino]phenylthio] butanoic acid | Rf 0.30 (CH$_2$Cl$_2$: EtOAc = 7:3) | ν 3600-2200, 1710, 1655, 1605, 1570, 1500, 1420, 1290, 760 |
| 3 (b) | $R^9 = R^{10} =$ 4-propylbenzyl | 4-[2-[4-[N,N-bis(4-propylbenzyl) amino]-2-methylbenzoylamino] phenylthio]butanoic acid | Rf 0.20 (hexane: EtOAc = 2:1) | ν 3600-2300, 1730, 1700, 1665, 1600, 1595, 1420, 1290, 1225, 1150, 760 |

TABLE VIII

Structure: R¹ and R² substituted benzamide with -NH-C(=O)- linked to phenyl-O-CH₂CH₂CH₂-COOH

| Example No. | R², R¹ | Name | TLC | IR(cm$^{-1}$) or mp |
|---|---|---|---|---|
| 4 (a) | R² = bis(4-propylphenyl)methoxy group (two 4-propylphenyl groups attached to CH-OMe); R¹ = H— | 4-[2-[4-[bis(4-propylphenyl)methoxy]benzoylamino]phenoxy]butanoic acid | Rf 0.32 (EtOAc: hexane: = 1:1) | ν (neat) 3470, 3100–2300, 1710, 1670, 1600, 1530, 1510, 1450, 1245, 1175, 1115, 1050, 760 |
| 4 (b) | R² = bis(4-propylphenyl)methoxy group; R¹ = CH₃— | 4-[2-[4-[bis(4-propylphenyl)methoxy]-2-methylbenzoylamino]phenoxy]butanoic acid | Rf 0.33 (EtOAc: hexane: = 1:1) | ν 3600–2300, 1700, 1655, 1600, 1520, 1450, 1250, 1050, 750 |
| 4 (c) | R² = bis(4-ethylphenyl)methoxy group; R¹ = H— | 4-[2-[4-[bis(4-ethylphenyl)methoxy]benzoylamino]phenoxy]butanoic acid | Rf 0.23 (EtOAc: hexane: = 1:1) | ν 3600–2300, 1705, 1600, 1505, 1450, 1240, 1170, 1000, 750 |
| 4 (d) | R² = bis(4-penthylphenyl)methoxy group; R¹ = H— | 4-[2-[4-[bis(4-penthylphenyl)methoxy]benzoylamino]phenoxy]butanoic acid | Rf 0.53 (EtOAc: hexane: = 1:1) | ν 3500–2300, 1700, 1660, 1600, 1500, 1440, 1240, 1170, 1000, 830, 740 |

TABLE VIII-continued

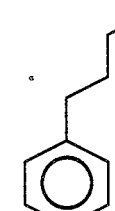

| Example No. | R², R¹ | Name | TLC | IR(cm⁻¹) or mp |
|---|---|---|---|---|
| 4 (e) | 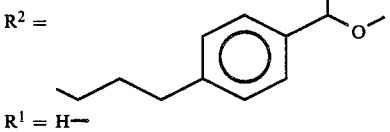$R^2 =$ <br> $R^1 = H-$ | 4-[2-[4-[bis(4-butylphenyl) methoxy]benzoylamino]phenoxy] butanoic acid | Rf 0.53 (EtOAc: hexane: = 1:1) | ν 3600–2300, 1705, 1600, 1505, 1450, 1250, 1170, 1010, 840, 760, 745 |
| 4 (f) | 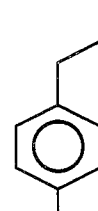$R^2 =$ <br> $R^1 = H-$ | 4-[2-[4-[bis(4-propylphenyl) methylthio]benzoylamino]phenoxy] butanoic acid | Rf 0.41 (EtOAc: hexane: = 2:1) | mp 109–111° C. |
| 4 (g) | 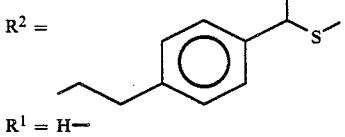$R^2 =$ <br> $R^1 = H-$ | 4-[2-[4-[bis(4-isobutylphenyl) methoxy]benzoylamino]phenoxy] butanoic acid | Rf 0.40 (EtOAc: hexane: = 1:1) | ν 3460, 3300~2300, 1710, 1600, 1500, 1450, 1240, 1170, 1005, 840, 760, 750 |
| 4 (h) | 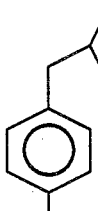$R^2 =$ <br> $R^1 = CH_3-$ | 4-[2-[4-[(α-methyl-4-isobutylphenyl)methoxy] benzoylamino]phenoxy] butanoic acid | Rf 0.35 (EtOAc: hexane: = 1:1) | ν 3600~2300, 1705, 1600, 1500, 1445, 1250, 1170, 840, 750 |

TABLE VIII-continued

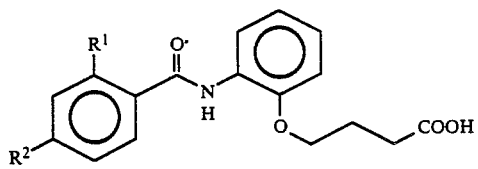

| Example No. | R², R¹ | Name | TLC | IR(cm⁻¹) or mp |
|---|---|---|---|---|
| 4 (i) | 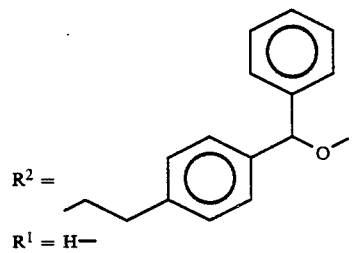  R¹ = H— | 4-[2-[4-[(α-phenyl-4-propylphenyl)methoxy]benzoylamino]phenoxy]butanoic acid | Rf 0.41 (EtOAc: hexane = 1:1) | ν 3450, 3100~2300, 1705, 1660, 1600, 1500, 1450, 1245, 1170, 1110, 895, 830, 745 |

EXAMPLE 5

Synthesis of 4-[2-[4-[N,N-bis(4-propylbenzyl)amino]-2-methylbenzoylamino]phenylsulfinyl]butanoic acid

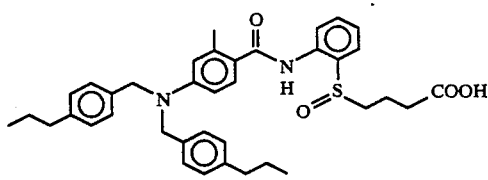

The aqueous solution (3.5 ml) of meta sodium periodate (137 mg) was added to the solution of methanol (13.5 ml) of the compound (260 mg; prepared in example 3(b)), and the mixture was stirred for 2 hours.

The aqueous solution (1 ml) of meta sodium periodate (45 mg) was added to the reaction mixture, and stirred for 12 hours.

The reaction solution was filtered off, dried, and azeotroped with toluene.

The residue was purified by column chromatography (CHCl₃-MeOH) to give the title compound (198 mg) having the following physical data.

TLC: Rf 0.15 (CH$_2$Cl$_2$: E$_t$OA$_c$=7:3);

IR: ν3600–2200, 1720, 1660, 1600, 1500, 1290, 1230, 1150, 760 cm⁻¹.

EXAMPLE 6(a)-6(c)

By the similar procedure as reference example 2, using the compounds prepared in reference example 10 and 11, on the other hand, by the similar procedure as reference example 9, 10 and example 1, the title compounds having the following physical data shown in Table IX were given.

TABLE IX

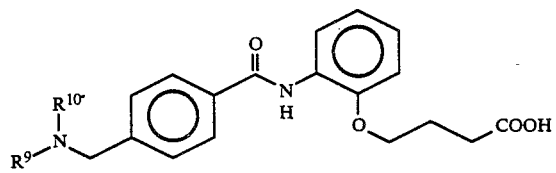

| Example No. | R⁹, R¹⁰ | Name | TLC | IR(cm⁻¹) or mp |
|---|---|---|---|---|
| 6 (a) | R⁹ = H—  R¹⁰ = 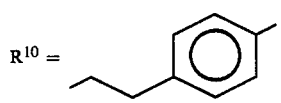 | 4-[2-[4-(4-propylphenylaminoethyl)benzoylamino]phenoxy]butanoic acid | Rf 0.24 (EtOAc: hexane: = 2:1) | mp 93–96° C. |
| 6 (b) | R⁹ = H—  R¹⁰ = 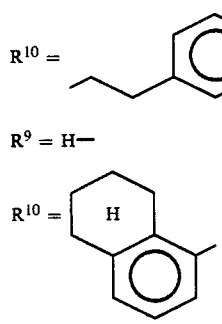 | 4-[2-[4-(5,6,7,8-tetrahydronaphthalene-1-yl)aminomethylbenzoylamino]phenoxy]butanoic acid | Rf 0.24 (EtOAc: hexane: = 2:1) | ν 3450, 3000–2300, 1710, 1590, 1520, 1445, 1250, 1040, 750 |

TABLE IX-continued

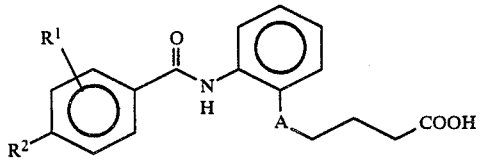

| Example No. | $R^9, R^{10}$ | Name | TLC | IR(cm$^{-1}$) or mp |
|---|---|---|---|---|
| 6 (c) | $R^9 = CH_3-$ <br> $R^{10} =$ 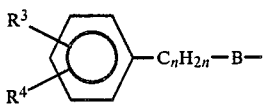 | 4-[2-[4-[N-methyl-N-(5,6,7,8,-tetrahydronaphthalene-1-yl) aminomethyl]benzoylamino]phenoxy] butanoic acid | Rf 0.39 (EtOAc: hexane: = 2:1) | mp 133° C. |

FORMULATION EXAMPLE

The following components were admixed in conventional method and punched out to obtain 100 tablets each containing 50 mg of active ingredient.

| | |
|---|---|
| 4-[2-[4-(4-isobutylphenylmethoxy)-benzoylamino]phenoxy] butanoic acid | 5 g |
| Cellulose calcium gluconate (disintegrating agent) | 0.2 g |
| Magnesium Stearate (lubricating agent) | 0.1 g |
| Microcrystaline cellulose | 4.7 g |

What is claimed is:

1. A benzoylaminophenoxybutanoic acid derivative of formula

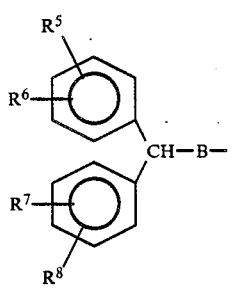 (I)

wherein
A is oxygen, sulfur or sulfinyl (SO) group,
$R^1$ is hydrogen or methyl,
$R^2$ is a group of the formula:

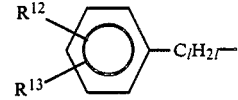 (i)

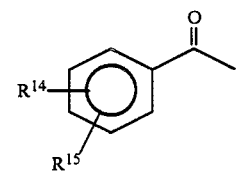 (ii)

-continued or

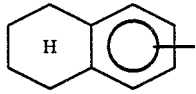 (iii)

wherein
B is oxygen, sulfur or a group of formula: $NR^{11}$,
wherein
$R^{11}$ is hydrogen or alkyl of from 1 to 4 carbon atoms;
$R^3$, $R^4$, $R^5$, $R^6$, $R^7$ and $R^8$ are, independently, hydrogen, alkyl of from 1 to 4 carbon atoms, halogen or trifluoromethyl;
m is 0 or 1;
n is an integer of from 1 to 4; and $R^9$ and $R^{10}$ are, independently, hydrogen, alkyl of from 1 to 5 carbon atoms or a group of formula:

wherein $R^{12}$, $R^{13}$, $R^{14}$ and $R^{15}$ are, independently, hydrogen, alkyl of from 1 to 4 carbon atoms, halogen or trifluoromethyl; and l represents an integer of from 1 to 4, with the proviso that $R^9$ and $R^{10}$ are not hydogen at the same time; or non-toxic salts thereof.

2. A compound according to claim 1, which is a compound of the formula:

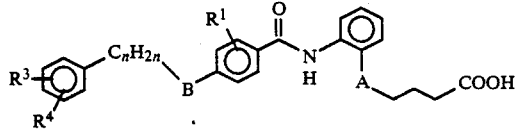

wherein all symbols have the same meaning as described in claim 1.

3. A compound according to either claim 1, or claim 2, wherein B is oxygen.

4. A compound according to either claim 1, or claim 2, which is:
 4-(2-(4-(4-isobutylphenylmethoxy)benzoylamino)-phenoxy)butanoic acid,
 4-(2-(4-benzyloxybenzoylamino)phenoxy)butanoic acid,
 4-(2-(4-(4-methylphenylmethoxy)benzoylamino)-phenoxy)butanoic acid,
 4-(2-(4-(4-ethylphenylmethoxy)benzoylamino)-phenoxy)butanoic acid,
 4-(2-(4-(4-propylphenylmethoxy)benzoylamino)-phenoxy)butanoic acid,
 4-(2-(4-(4-isopropylphenylmethoxy)benzoylamino)-phenoxy)butanoic acid,
 4-(2-(4-(3-phenylpropoxy)benzoylamino)phenoxy)-butanoic acid,
 4-(2-(4-(4-phenylbutoxy)benzoylamino)phenoxy)-butanoic acid,
 4-(2-(4-(4-isobutylphenylmethoxy)-2-methylbenzoylamino)phenoxy)butanoic acid
or
 4-(2-(4-(4-isobutylphenylmethoxy)-3-methylbenzoylamino)phenoxy)butanoic acid.

5. A compound according to either claim 1, or claim 2, wherein B is the group of the formula: $NR^{11}$, wherein $R^{11}$ is hydrogen or alkyl of from 1 to 4 carbon atoms.

6. A compound according to either claim 1, or claim 2, which is:
 4-(2-(4-(4-isobutylbenzylamino)benzoylamino)-phenoxy)butanoic acid,
 4-(2-(4-(4-isobutylbenzylamino)-2-methylbenzoylamino)phenoxy)butanoic acid,
 4-(2-(4-(4-propylbenzylamino)-2-methylbenzoylamino)phenoxy)butanoic acid,
 4-(2-(4-(1-(4-isobutylphenyl)ethylamino)-2-methylbenzoylamino)phenoxy)butanoic acid,
 4-(2-(4-(4-isopropybenzylamino)-2-methylbenzoylamino)phenoxy)butanoic acid,
 4-(2-(4-(4-propylbenzylamino)-2-methylbenzoylamino)phenylthio)butanoic acid
or
 4-(2-(4-(2-trifluoromethylbenzylamino)-2-methylbenzoylamino)phenoxy)butanoic acid.

7. A compound according to claim 1, which is a compound of the general formula:

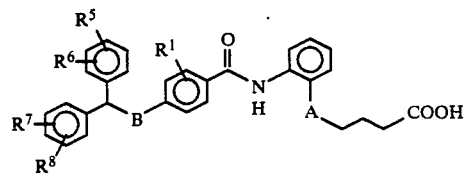

wherein all symbols have the same meaning as described in claim 1.

8. A compound according to either claim 1, or claim 7, wherein B is oxygen.

9. A compound according to either claim 1, or claim 7, which is:
 4-(2-(4-(bis(4-propylphenyl)methoxy)benzoylamino)-phenoxy)butanoic acid,
 4-(2-(4-(bis(4-propylphenyl)methoxy)-2-methylbenzoylamino)phenoxy)butanoic acid,
 4-(2-(4-(bis(4-ethylphenyl)methoxy)benzoylamino)-phenoxy)butanoic acid,
 4-(2-(4-(bis(4-pentylphenyl)methoxy)benzoylamino)-phenoxy)butanoic acid
or
 4-(2-(4-(bis(4-butylphenyl)methoxy)benzoylamino)-phenoxy)butanoic acid.

10. A compound according to either claim 1, or claim 7, wherein B is the group of the formula: $NR^{11}$, wherein $R^{11}$ has the same meaning as described in claim 1.

11. A compound according to either claim 1, or claim 7, which is:
 4-(2-(4-(bis(4-propylphenyl)methylamino)-2-methylbenzoylamino)phenoxy)butanoic acid
 4-(2-(4-(bis(4-propylphenyl)methylamino)benzoylamino)phenoxy)butanoic acid,
or
 4-(2-(4-(N-bis(4-propylphenylmethyl-N-methylamino)benzoylamino)phenoxy)butanoic acid.

12. A compound according to either claim 1, or claim 7, wherein B is sulfur.

13. A compound according to either claim 1, or claim 7, which is:
 4-(2-(4-(bis(4-propylphenyl)methylthio)benzoylamino)phenoxy)butanoic acid.

14. A compound according to claim 1, which is a compound of the formula:

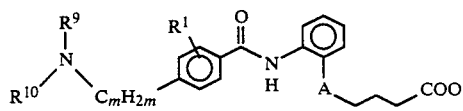

wherein all symbols have the same meaning as described in claim 1.

15. A compound according to either claim 1, or claim 14, wherein $R^1$ is hydrogen.

16. A compound according to either claim 1, or claim 14, which is:
 4-(2-(4-(N,N-bis(4-propylbenzyl)amino)benzoylamino)phenoxy)butanoic acid,
 4-(2-(4-(4-propylphenylaminomethyl)benzoylamino)-phenoxy)butanoic acid,
 4-(2-(4-(5,6,7,8-tetrahydronaphthalene-1-yl)aminomethylbenxoylamino)phenoxy)butanoic acid
or
 4-(2-(4-(N-methyl-N-(5,6,7,8-tetrahydronaphthalene-1-yl)aminomethyl)benzoylamino)phenoxy)-butanoic acid.

17. A compound according to either claim 1, or claim 14, wherein $R^1$ is methyl.

18. A compound according to either claim 1, or claim 14, which is:
 4-(2-(2-methyl-4-(N,N-bis(4-propylbenzyl)amino)-benzoylamino)phenoxy)butanoic acid,
 4-(2-(4-(N,N-bis(4-isobutylbenzyl)amino)-2-methyl-benzoylamino)phenoxy)butanoic acid, 4-(2-(4-(N,N-dipentylamino)-2-methylbenzoylamino)phenoxy)butanoic acid, 4-(2-(4-(N-pentyl-N-(4-propylbenzyl)amino)-2-methylbenzoylamino)phenoxy)butanoic acid, 4-(2-(4-(N-methyl-N-(4-propylbenzyl)amino)-2-methylbenzoylamino)phenoxy)butanoic acid, 4-(2-(4-(N,N-bis(4-phenylbutyl)amino)-2-methylbenzoylamino)phenoxy)butanoic acid, 4-(2-(4-(N,N-bis(4-isopropylbenzyl)amino-2-methylbenzoylamino)phenoxy)butanoic acid, 4-(2-(4-(N,N-bis(4-propylbenzyl)amino)-2-methylbenzoylamino)phenylthio)butanoic acid, 4-(2-(4-(N,N-bis(4-propylbenzyl)amino)-2-methylbenzoylamino)phenylsulfinyl)butanoic acid, 4-(2-(4-(N,N-bis(2,4-difluorobenzyl)amino)-2-methylbenzoylamino)phenoxy)butanoic acid, 4-(2-(4-(N-(4-propylbenzyl)-N-(4-propylbenzoyl)amino)-2-methylbenzoylamino)phenoxy)butanoic acid, 4-(2-(4-(N,N-bis(2-trifluoromethylbenzyl)amino)-2-methylbenzoylamino)phenoxy)butanoic acid or 4-(2-(4-(N,N-bis(4-trifluoromethylbenzyl)amino)-2-methylbenzoylamino)phenoxy)butanoic acid.

19. A process for the preparation of benzoylaminophenoxybutanoic acid derivatives of the formula:

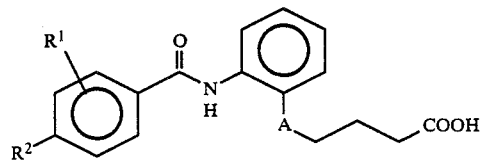

wherein

A is oxygen, sulfur or sulfinyl (SO) group;

$R^1$ is hydrogen or methyl;

$R^2$ is a group of the formula:

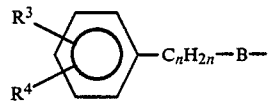  (i)

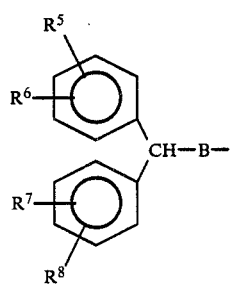  (ii)

or

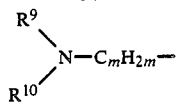  (iii)

wherein

B is oxygen, sulfur or a group of formula: $NR^{11}$, wherein $R^{11}$ is hydrogen or alkyl of from 1 to 4 carbon atoms;

$R^3$, $R^4$, $R^5$, $R^6$, $R^7$ and $R^8$ are, independently, hydrogen, alkyl of from 1 to 4 carbon atoms, halogen or trifluoromethyl;

m is 0 or 1;

n is an integer of from 1 to 4; and $R^9$ and $R^{10}$ are, independently, hydrogen, alkyl of from 1 to 5 carbon atoms or a group of formula:

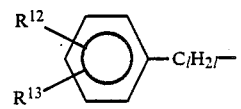

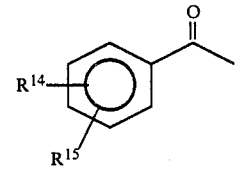

or

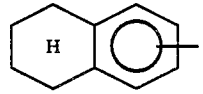

wherein $R^{12}$, $R^{13}$, $R^{14}$ and $R^{15}$ are, independently, hydrogen, alkyl of from 1 to 4 carbon atoms, halogen or trifluoromethyl; and l represents an integer of from 1 to 4, with the proviso that $R^9$ and $R^{10}$ are not hydrogen at the same time; the process consisting of saponifying a compound of the formula:

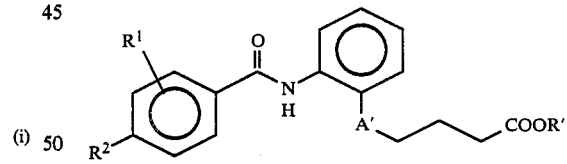  (II)

wherein R' is alkyl of from 1 to 4 carbon atoms, A' is oxygen, sulfur or a group of formula: $NR^{11}$, wherein $R^{11}$ has the same meaning as defined hereinbefore, and other symbols are the same as defined hereinbefore; or consisting of oxidizing a compound of the formula:

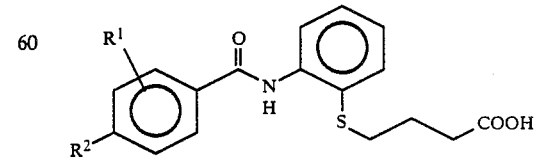  (Ib)

wherein all symbols have the same meaning as defined hereinbefore.

* * * * *